US012653547B2

(12) United States Patent (10) Patent No.: US 12,653,547 B2
Amesbury et al. (45) Date of Patent: Jun. 16, 2026

(54) UNICONDYLAR INSTRUMENTS AND PROCEDURES

(71) Applicant: DEPUY IRELAND UNLIMITED COMPANY, County Cork (IE)

(72) Inventors: Kevin M Amesbury, Leeds (GB); James E Barnett, Leeds (GB); Andrew Dixon, Leeds (GB)

(73) Assignee: DEPUY IRELAND UNLIMITED COMPANY, Ringaskiddy (IE)

( * ) Notice: Subject to any disclaimer, the term of this patent is extended or adjusted under 35 U.S.C. 154(b) by 471 days.

(21) Appl. No.: 18/184,549

(22) Filed: Mar. 15, 2023

(65) Prior Publication Data

US 2024/0307072 A1     Sep. 19, 2024

(51) Int. Cl.
    *A61B 17/15*          (2006.01)
(52) U.S. Cl.
    CPC .................................. *A61B 17/157* (2013.01)
(58) Field of Classification Search
    CPC ...................................................... A61B 17/157
    See application file for complete search history.

(56) References Cited

U.S. PATENT DOCUMENTS

| | | | | |
|---|---|---|---|---|
| 4,759,350 A | * | 7/1988 | Dunn ................. | A61B 17/2812 |
| | | | | 606/82 |
| 6,413,261 B1 | * | 7/2002 | Grundei ............... | A61B 17/155 |
| | | | | 606/88 |
| 8,425,523 B2 | * | 4/2013 | Aram ................. | A61B 17/1764 |
| | | | | 606/88 |
| 10,709,458 B1 | * | 7/2020 | Bini ...................... | A61B 17/157 |
| 2002/0198531 A1 | * | 12/2002 | Millard ............... | A61B 17/154 |
| | | | | 606/87 |
| 2003/0171757 A1 | * | 9/2003 | Coon ................... | A61B 17/157 |
| | | | | 606/87 |
| 2003/0225413 A1 | * | 12/2003 | Sanford ............... | A61B 17/155 |
| | | | | 606/87 |
| 2004/0015173 A1 | * | 1/2004 | Irving ................. | A61B 17/157 |
| | | | | 606/88 |
| 2004/0153086 A1 | * | 8/2004 | Sanford ............... | A61F 2/4684 |
| | | | | 606/88 |
| 2005/0171545 A1 | * | 8/2005 | Walsh ................. | A61B 17/154 |
| | | | | 606/88 |
| 2005/0256527 A1 | | 11/2005 | Delfosse | |

(Continued)

OTHER PUBLICATIONS

GB Search Report From Corresponding GB Patent Application GB2203670.1 Dated Aug. 25, 2022, 1 Page.

*Primary Examiner* — David W Bates

(57) ABSTRACT

Instrumentation and a method for unicompartmental knee replacement procedure are described. The surgical instrumentation may include a unicondylar posterior femoral cutting guide, a unicondylar tibial cutting block assembly and a unicondylar femoral cutting guide. The method may include inserting the unicondylar posterior femoral cutting guide into a joint gap while the knee is in flexion, resecting the posterior femoral condyle of the femur while the knee is in flexion, the surface of the resected posterior femoral condyle defining a reference plane, and setting the position of a unicondylar tibial cutting block on the tibia relative to the reference plane by using the resected surface of the posterior femoral condyle. The unicondylar femoral cutting guide may then be used to make one or more femoral cuts.

10 Claims, 5 Drawing Sheets

(56) References Cited

U.S. PATENT DOCUMENTS

| | | | |
|---|---|---|---|
| 2006/0064105 A1* | 3/2006 | Raistrick | A61B 17/154 606/87 |
| 2006/0247646 A1* | 11/2006 | Bihary | A61B 17/157 606/87 |
| 2007/0173849 A1* | 7/2007 | Claypool | A61B 17/157 606/87 |
| 2008/0015605 A1* | 1/2008 | Collazo | A61B 17/157 606/87 |
| 2008/0015606 A1 | 1/2008 | D'Alesso et al. | |
| 2008/0015607 A1* | 1/2008 | D'Alessio | A61F 2/4684 606/87 |
| 2008/0172054 A1* | 7/2008 | Claypool | A61B 17/157 606/87 |
| 2008/0183176 A1* | 7/2008 | Canonaco | A61B 17/157 606/87 |
| 2008/0195110 A1 | 8/2008 | Plassy | |
| 2009/0043310 A1* | 2/2009 | Rasmussen | A61B 17/1764 606/88 |
| 2009/0222014 A1* | 9/2009 | Bojarski | A61B 17/1615 606/88 |
| 2009/0264890 A1* | 10/2009 | Duggineni | A61B 17/157 606/88 |
| 2010/0010493 A1* | 1/2010 | Dower | A61B 17/157 606/87 |
| 2011/0106092 A1* | 5/2011 | Fisher | A61B 17/157 606/88 |
| 2011/0196377 A1* | 8/2011 | Hodorek | A61B 17/157 606/87 |
| 2012/0078263 A1* | 3/2012 | Parisi | A61F 2/3859 623/20.14 |
| 2012/0184961 A1* | 7/2012 | Johannaber | A61B 17/157 606/88 |
| 2012/0209275 A1* | 8/2012 | Fox | A61B 17/1764 606/88 |
| 2013/0204258 A1* | 8/2013 | Goodfellow | A61F 2/3868 606/88 |
| 2014/0257310 A1* | 9/2014 | Trachsler | A61B 17/157 606/88 |
| 2017/0007273 A1* | 1/2017 | Freiberg | A61B 17/1764 |
| 2017/0348008 A1 | 12/2017 | Lavallee et al. | |
| 2018/0140440 A1* | 5/2018 | Jackson | A61F 2/4684 |
| 2019/0167275 A1* | 6/2019 | Horta | A61B 17/157 |
| 2019/0357920 A1* | 11/2019 | Nonnenmann | A61B 17/154 |
| 2020/0155168 A1* | 5/2020 | Minfelde | A61F 2/4684 |
| 2021/0259713 A1* | 8/2021 | Trabish | A61B 90/94 |
| 2021/0290252 A1* | 9/2021 | Oh | A61B 17/155 |
| 2022/0096247 A1* | 3/2022 | Wang | A61F 2/461 |
| 2022/0110637 A1* | 4/2022 | Boettiger | A61B 17/157 |

* cited by examiner

Figure 3
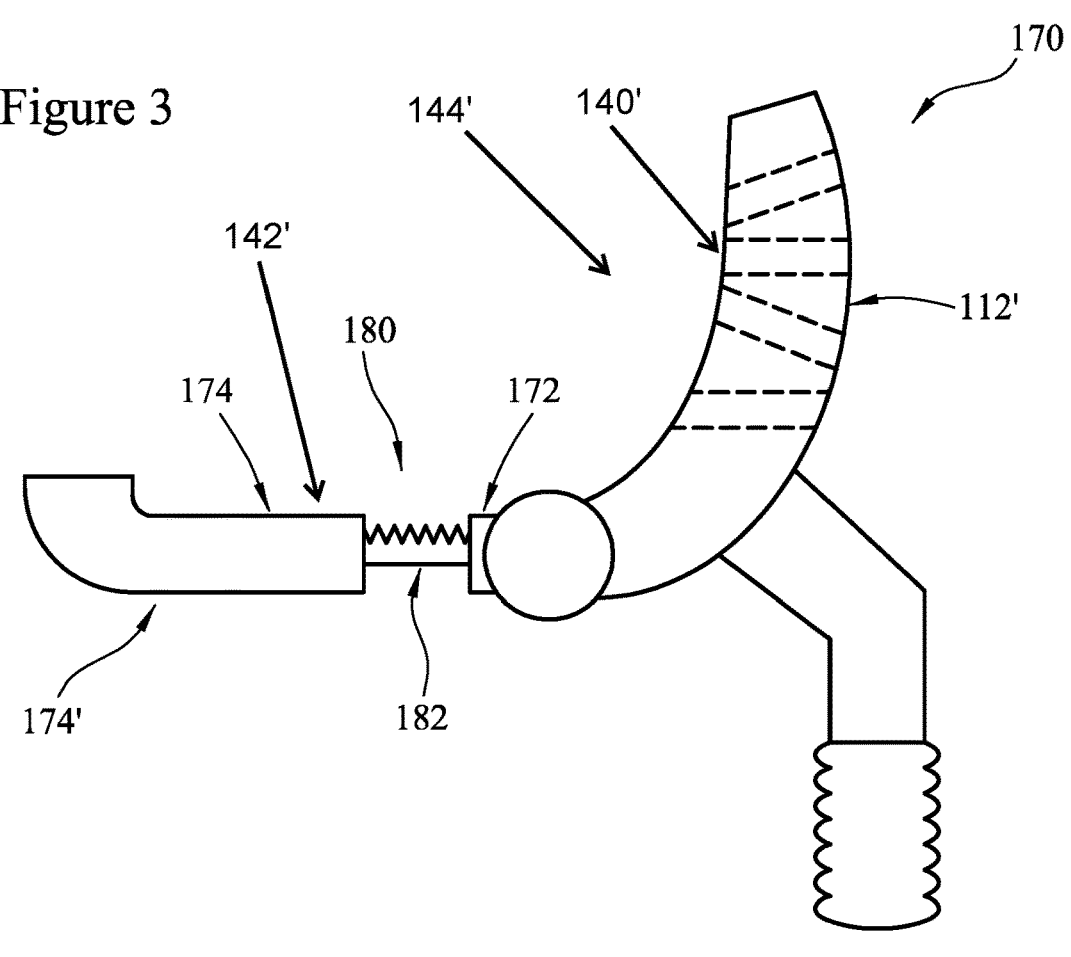
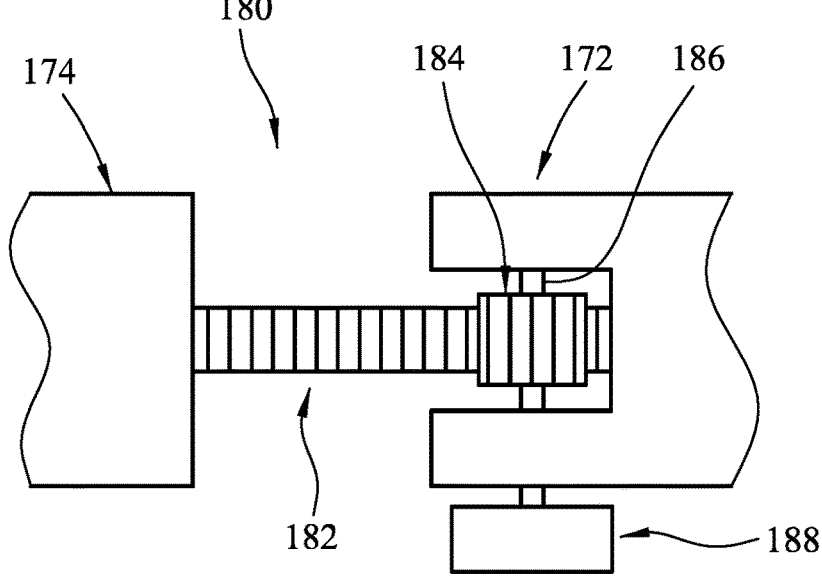
Figure 4

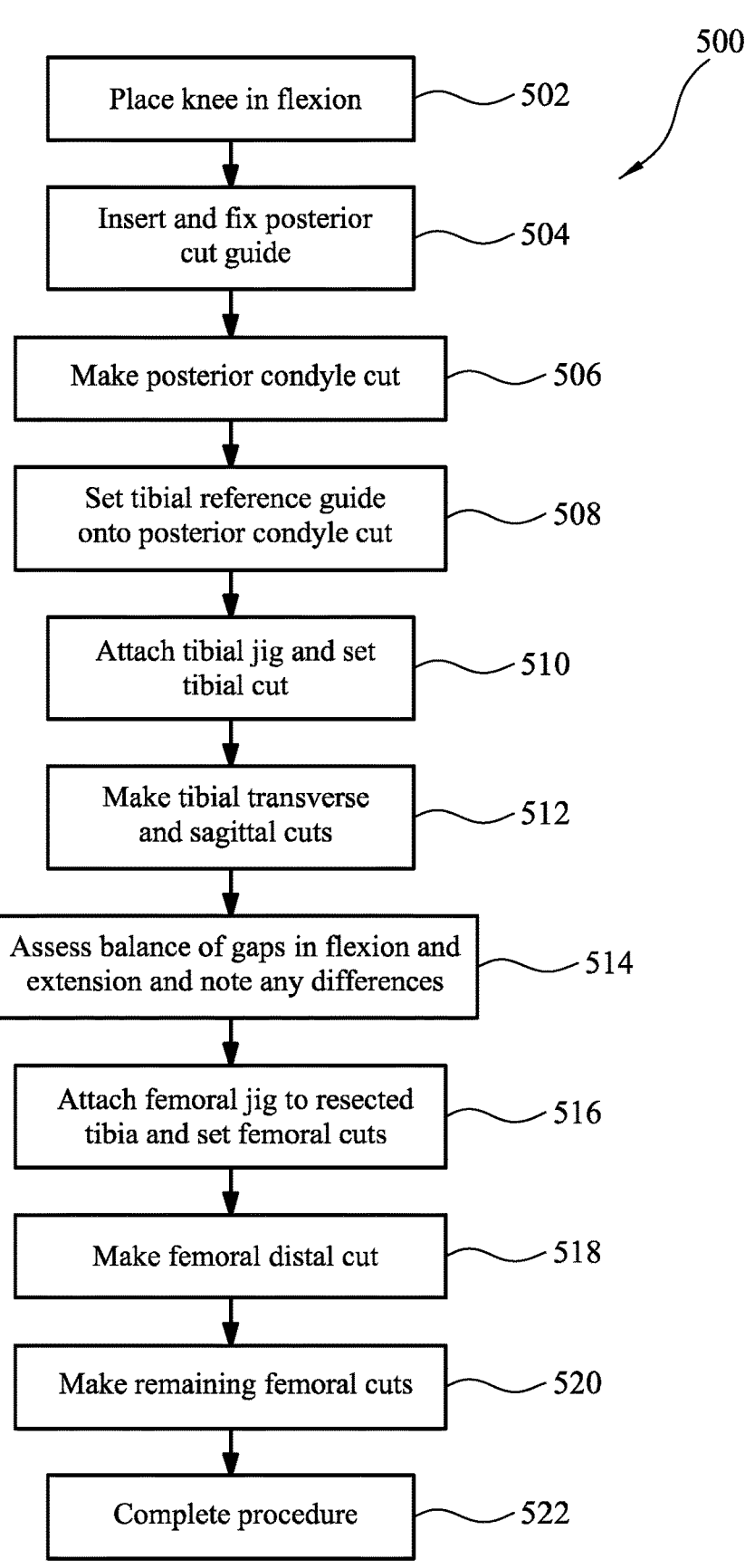

500

Place knee in flexion — 502

Insert and fix posterior cut guide — 504

Make posterior condyle cut — 506

Set tibial reference guide onto posterior condyle cut — 508

Attach tibial jig and set tibial cut — 510

Make tibial transverse and sagittal cuts — 512

Assess balance of gaps in flexion and extension and note any differences — 514

Attach femoral jig to resected tibia and set femoral cuts — 516

Make femoral distal cut — 518

Make remaining femoral cuts — 520

Complete procedure — 522

Figure 7

UNICONDYLAR INSTRUMENTS AND PROCEDURES

This application claims priority to Great Britain Patent Application No. 2203670.1, entitled "Unicondylar Instruments and Procedures" and filed on Mar. 16, 2022. The entirety of that application is incorporated herein by reference.

TECHNICAL FIELD

The present disclosure relates to surgical instruments and methods, and in particular to surgical instruments and methods for use in a partial knee replacement procedure.

BACKGROUND

There are two general types of knee replacement procedures. A first is total knee replacement (TKR) procedures in which both condyles and the entire proximal tibia are replaced with respective prosthetic components to replace the entire knee. A second is partial or unicompartmental knee replacement procedures in which only a one of the condyles of the femur and the corresponding part of the proximal tibia, either the medial part or the lateral part, are replaced with respective prosthetic components.

An aspect of both types of procedure is making tibial cuts which largely define the position of the tibial prosthetic components on the tibia and the making of femoral cuts which largely define the position of the femoral prosthetic component relative to the femur. Often, cutting blocks are used to aid the making of such cuts and include some kind of guide to help guide a cutting instrument such as a powered bone saw or similar. The cutting block is attached to the bone at some position and the position of the cutting block largely defines where the cut is made, although some cutting blocks can also include adjustment mechanisms to allow the guide to move relative to the bone.

The positioning of the cuts is an important factor in the success of a knee replacement procedure and there are numerous degrees of freedom including the position of the tibial cuts relative to the tibia, the position of the femoral cuts relative to the femur and then the positions of the tibial and femoral cuts relative to each other.

Various approaches can be used to try and appropriately position cutting blocks relative to the bone that they are to be used to cut or resect. Some of these may use native anatomical features of the bone to serve as a datum relative to which the cutting block may be positioned and other may use a previously made cuts to serve as a datum relative to which other cutting blocks may be positioned.

In a conventional unicondylar knee replacement procedure the tibial cuts may be made first, before resecting the femur, by attaching a tibial jig to the patient's femur and then using the tibial jig to position and then attached a tibial cutting guide relative to the native anatomy of the patient's tibia before making the tibial transverse and sagittal cuts.

SUMMARY

The present disclosure is directed to surgical instruments, apparatus, kits of parts and methods relating to unicondylar knee replacement procedures which may improve the reliability with which tibial cuts or femoral cuts or tibial cuts and femoral cuts may be made as part of a unicondylar knee replacement procedure.

A first aspect of the present disclosure provides a unicondylar posterior femoral cutting guide comprising: a body having an anterior portion and a base, wherein the anterior portion and the base define a curved inner surface and wherein the anterior portion defines a slot arranged to guide a unicondylar posterior femoral cut; and a handle attached to the body, wherein the handle extends forwardly of the body and is manipulable by a user to insert the base within a joint gap of a knee of a patient.

The anterior portion may define a plurality of apertures there through for receiving respective bone pins to permit fixation of the cutting guide to a femur of the patient in use.

The plurality of apertures may comprise a first aperture, a second aperture and a third aperture, and wherein the first aperture and second aperture are parallel to each other and the third aperture is inclined relative to the first and second apertures.

The base may have a first thickness and the anterior portion may have a second thickness and wherein the first thickness may be less than the second thickness.

The first thickness may be in the range of 2 mm to 3 mm.

A region of the curved inner surface of the base may define a minimum position, the slot may define a cutting plane and wherein a separation between the minimum position and the cutting plane in a direction generally perpendicular to the cutting plane may define a resection height of the posterior femoral condyle.

The separation may be in the range of approximately 4 mm to 8 mm. The separation may be in the range of approximately 6 mm to 7 mm.

The base may include a tail portion at a free end of the base. The tail portion may be inclined relative to an adjacent portion of the remainder of the base and may extend at least partially in an upward direction relative to the remainder of the base.

The base may be a curved base.

The handle may be releasably attachable to the body.

A further aspect of the disclosure provides a kit of surgical instrumentation comprising a plurality of unicondylar posterior femoral cutting guides according to the first aspect and wherein each unicondylar femoral cutting guide has a different size in an anterior-posterior direction, or a medial-lateral direction, or both an anterior-posterior direction and a medial-lateral direction.

A second aspect of the disclosure provides instrumentation for a unicondylar knee replacement procedure, comprising: a tibial reference guide; and a tibial jig, wherein the tibial reference guide comprises an anterior portion having a curved inner surface, a base extending from the anterior portion and having a flat upper surface defining a reference plane and a coupling mechanism for connecting the tibial reference guide to the tibial jig, wherein the tibial jig includes a support attachable to a tibia of a patient, an attachment formation for attaching a unicondylar tibial cutting block and a coupling member arranged to connect to the coupling mechanism, and wherein the tibial reference guide and the tibial jig provide between them a first adjustment mechanism arranged and configured to adjust the separation between the tibial reference guide and the tibial jig in a direction perpendicular to the reference plane when the tibial reference guide and tibial jig are connected together.

The anterior portion may define a plurality of apertures there through for receiving respective bone pins to permit fixation of the tibial reference guide to a femur of the patient in use.

3

The plurality of apertures may comprise a first aperture, a second aperture and a third aperture. The first aperture and the second aperture may be parallel to each other and the third aperture may be inclined relative to the first and second apertures.

The first adjustment mechanism may comprise a housing, an elongate member which is slidable relative to the housing, and a releasable lock which is operable to set the position of the elongate member relative to the housing.

The housing may include a scale and the elongate member may include an indicium adjacent the scale and arranged to indicate a current separation value for a current position of the elongate member relative to the housing.

The first adjustment mechanism may be provided as part of the tibial reference guide.

The first adjustment mechanism may be attached to the base of the tibial reference guide and may be positioned to the side of the rest of the tibial reference guide.

The tibial reference guide and the tibial jig may provide between them a second adjustment mechanism arranged and configured to adjust the varus-valgus angle of the tibial jig relative to the tibial reference guide.

The tibial reference guide and the tibial jig may provide between them a third adjustment mechanism arranged and configured to adjust the medial-lateral position of the tibial jig relative to the tibial reference guide.

The tibial reference guide and the tibial jig may provide between them a fourth adjustment mechanism arranged and configured to adjust the anterior-posterior slope angle of the tibial jig relative to the tibial reference guide.

A third aspect of the disclosure provides a unicondylar femoral cutting guide comprising: a base having a flat under surface defining a plane and having a handle extending forwardly of the base; a post extending upwardly from the base in a direction perpendicular to the plane, wherein the post defines a first inclined aperture there through, the first inclined aperture providing a first cutting guide for a first femoral chamfer cut; and a member coupled to a free end of the post and extending in a direction generally parallel to the plane, wherein the member defines a third aperture there through providing a third cutting guide for a distal femoral cut.

The post may further define a second inclined aperture there through, the second inclined aperture providing a second cutting guide for a second femoral chamfer cut.

The member may be translatable relative to the post.

The member may include a first scale indicating an amount of distalisation of the distal femoral cut and/or may include a second scale indicating an amount of proximalisation of the distal femoral cut.

The post may be releasably attachable to the base.

A further aspect of the disclosure provides a kit of surgical instrumentation comprising: the unicondylar femoral cutting guide of the third aspect; and a plurality of posts, wherein each post has a different length and different relative positions of the first inclined aperture and the second inclined aperture along the longitudinal axis of the post which correspond to different sized prosthetic unicondylar femoral implants.

A further aspect of the disclosure provides a kit of surgical instrumentation for a unicondylar knee replacement procedure comprising: the unicondylar posterior femoral cutting guide of the first aspect; the instrumentation of the second aspect; and/or the unicondylar femoral cutting guide of the third aspect.

A further aspect of the disclosure provides a method for a unicondylar knee replacement procedure comprising:

inserting a unicondylar posterior femoral cutting guide into a joint gap between a femur and a tibia of a knee of a patient while the knee is in flexion;

using the unicondylar posterior femoral cutting guide to resect the posterior femoral condyle of the femur while the knee is in flexion, wherein the surface of the resected posterior femoral condyle defines a reference plane; and setting the position of a unicondylar tibial cutting block on the tibia relative to the reference plane by using the resected surface of the posterior femoral condyle.

The method may further comprise selecting a unicondylar posterior femoral cutting guide from a plurality of unicondylar posterior femoral cutting guides each having a different size in the anterior-posterior direction or medial-lateral direction, wherein the selected unicondylar posterior cutting guide most closely matches the size of the femur of the patient.

Setting the position of the unicondylar tibial cutting block may include one or more of: adjusting the position of the unicondylar tibial cutting block in a direction perpendicular to the reference plane to set the transverse tibial cut height; adjusting the medial-lateral position of the unicondylar tibial cutting block to set the medial-lateral position on the tibia; adjusting the varus-valgus angle of the unicondylar tibial cutting block to set the varus valgus angle of the transverse tibial cut; and adjusting the anterior-posterior slope angle of the unicondylar tibial cutting block to set the anterior-posterior slope of the transverse tibial cut.

The method may further comprise: using the unicondylar tibial cutting block at the set position on the tibia to make a transverse tibial cut and a sagittal tibial cut; and assessing the joint gap between the femur and the resected tibia for the knee in flexion and in extension.

The method may further comprise: positioning a femoral cutting guide on the resected tibia; and using a distal femoral cut guide of the femoral cutting guide to make a distal femoral cut with the knee in flexion.

The method may further comprise: adjusting the position of the distal femoral cut guide relative to the femoral cutting guide to distalise the distal femoral cut position if the flexion gap is less than the extension gap or to proximalise the distal femoral cut position if the extension gap is less than the flexion gap.

The method may further comprise: using a first chamfer cut guide of the femoral cutting guide to make a first chamfer cut to the femur; and/or using a second chamfer cut guide of the femoral cutting guide to make a second chamfer cut to the femur.

BRIEF DESCRIPTION OF THE DRAWINGS

Embodiments will now be described in detail, by way of example only, and with reference to the accompanying drawings, in which:

FIG. 3 shows a side elevation of a further unicondylar posterior femoral cutting guide;

FIG. 4 shows a plan view of an expanded detail of the adjustment mechanism of the further unicondylar cutting guide shown in FIG. 3;

FIG. 7 shows a flow chart illustrating some of a partial knee replacement procedure and illustrating methods of using the surgical instrumentation shown in FIGS. 1 to 6.

In the Figures of drawings, like items in the different Figures share common reference signs unless indicated otherwise.

DETAILED DESCRIPTION

The instrumentation and methods described herein are configured to permit a flexion first unicondylar knee replacement procedure to be carried out in which a first cut is made to the posterior condyle of the femur with the knee in flexion. In many cases, the articulating surface of the posterior condyle of the femur will be in a good state and so provides a good anatomical reference relative to which a first cut can be made. The resulting resected surface of the posterior femur may then be used as a reference datum relative to which other cuts may be made to both the tibia and the femur using instrumentation described herein. This is in contrast to other unicondylar knee replacement procedures, and instrumentation configured to be used in such procedures, in which the native tibia is used as an anatomical datum relative to which the tibial cuts are made. In many cases the native tibia of the patient's knee will be worn or may be diseased, or otherwise impaired, and so may present a less reliable anatomical datum relative to which the tibial cuts may be made.

Figures 1, 2:
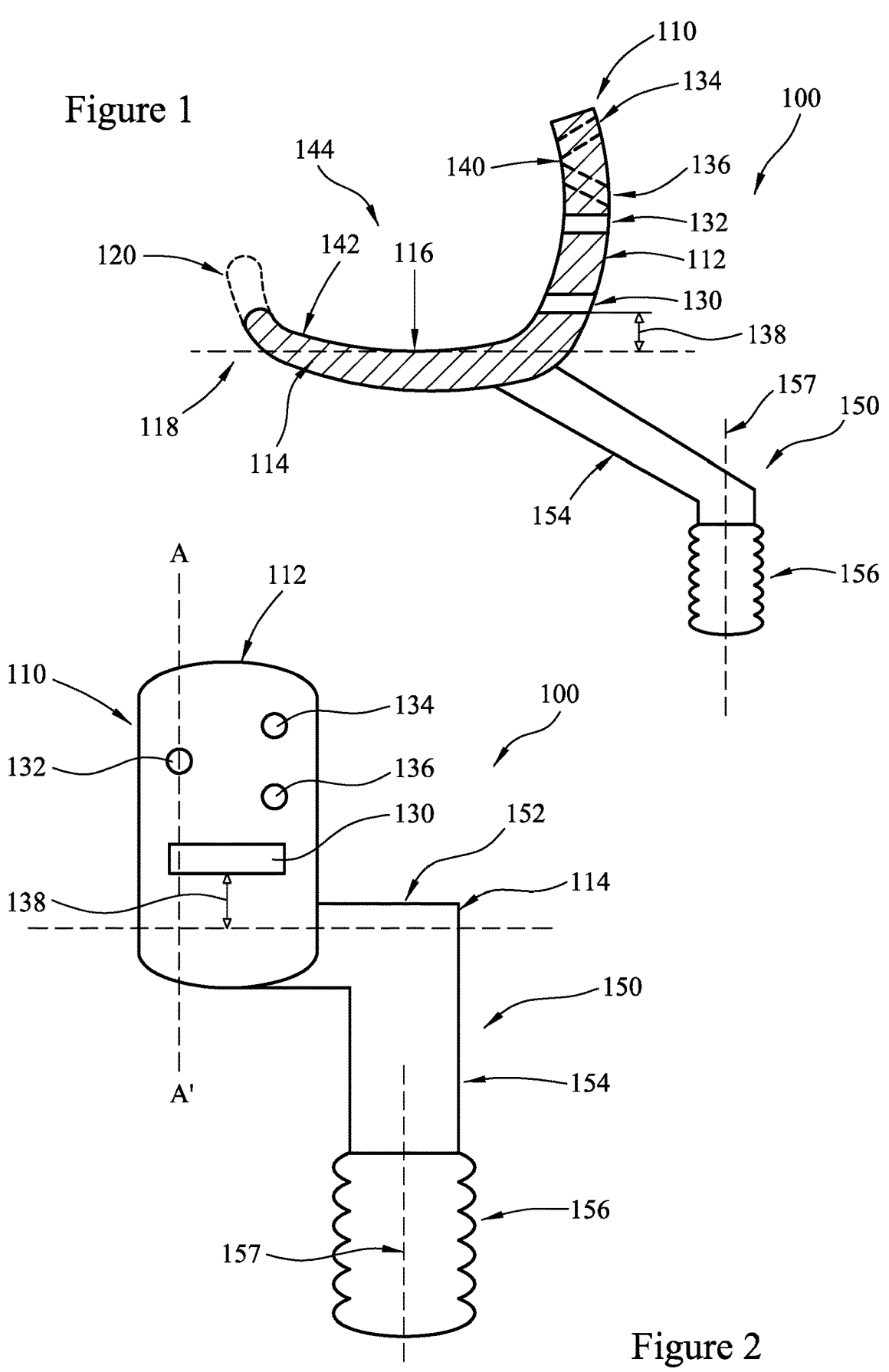
FIG. 1 shows a side elevation of a unicondylar posterior femoral cutting guide.
FIG. 2 shows a front elevation of the unicondylar posterior femoral cutting guide shown in FIG. 1.

With reference to FIG. 1 there is shown a cross-sectional view of a unicondylar posterior femoral cutting guide 100. FIG. 2 shows an elevation of the front of the unicondylar posterior femoral cutting guide 100. The cross-section of FIG. 1 is approximately along line A-A' of FIG. 2. The unicondylar posterior femoral cutting guide 100 general comprises a curved body part 110 and a handle part 150.

The curved body 110 generally has a curved anterior portion 112 and a base portion 114 which is generally flatter than the base portion. The base portion has a generally lowest, or minimum, curved surface region at a position indicated by asterisk 116. Dashed line 118 illustrates the position of the minimum surface region 116 relative to other parts of the body 110. Minimum surface region 116 provides a datum on which a point on the posterior condyle of a femur will sit flat, or flush, in use. The base portion 114 may optionally have a tail portion 120 extending from a distal end thereof and directed generally upwardly relative to the rest of the base portion 114. The base portion 114, and tail 120 when provided, are generally thinner than the anterior portion 112 of the body 110. The base, and tail, may have a thickness in the range of about 1 mm to 3 mm, for example approximately 2 mm, so that they may easily be introduce into the native gap joint between the native tibia and posterior native condyle of the femur, with the femur in flexion.

The curved anterior portion 112 defines a first aperture 130 having a generally rectangular shape and which provides a posterior femoral condyle cutting guide for receiving a cutting instrument such as a chisel or saw blade or similar. The curved anterior portion 112 also defines first to third pin holes 132, 134, 136 for receiving bone pins to secure the cutting guide 100 to a patient's femur in use. First pin hole 132 and second pin hole 134 are straight and parallel to each other, whereas third pin hole 136 is inclined or divergent relative to the first two pin holes to improve fixation in use.

As best illustrated in FIG. 1, the separation 138 between the minimum region 116 and a lower surface of the cutting guide 130 defines the size of the posterior femoral cut and may be approximately 6.5 mm. This separation corresponds to the thickness of the posterior condyle of the prosthetic implant, and which may be generally consistent across difference sizes of the implant system. The anterior portion 112 may be thicker than the base portion 114 as it does not need to be located within the joint gap and its relatively greater thickness may improve the stability of pinning and/or the cut guiding action.

A curved surface 140 of the anterior portion 112 is curved and is generally dimensioned to match the curvature of the distal condyle of a native femur. The curved surface 140 and upper curved surface 142 of base 114 generally defines a concave space 144 dimensioned and configured to receive the distal and posterior portions of the condyle of a native femur. As will be appreciated native human femurs may have a range of sizes and therefore a range of sizes of cutting guide 100 may be provided, for example six different sizes. The greatest difference between different sized guides may the length of the base portion 114 and the position of the minimum region 116 to ensure that the posterior condyle may be received and seated on the minimum region. In embodiments in which the tail portion 120 is provided, the distance between the tail portion 120 and the anterior portion 112 will generally increase with the size of the guide in order to accommodate increasingly larger posterior condyles.

With reference to FIGS. 3 and 4 there is shown a side view of a further unicondylar posterior femoral cutting guide 170 generally similar to that shown in FIGS. 1 and 2. The further cutting guide 170 includes an adjustment mechanism 180 which is shown in plan view in FIG. 4.

The base portion 114' includes an anterior part 172 and a separate posterior part 174 which is movable relative to the anterior portion 112' so as to provide a size adjustable cutting guide. The posterior portion 174 of the base 114' is connected to the anterior part 172 by a toothed member 182. Toothed member 182 passes below a rotatable toothed wheel 184 which is borne upon an axle 186 having a knob 188 attached to an external free end of the axle 186, as best illustrated in FIG. 4. Hence, knob 188 may be rotated by a user to operate the adjustment mechanism 180 which generally has the form of a rack and pinion. However, other adjustment mechanisms which permit adjustment of the length of the base may be used. The adjustment mechanism may include a ratchet or other locking mechanism so that the size of the cutting guide to be selected and temporarily set.

Similarly to the embodiment shown in FIGS. 1 and 2, a curved surface 140' of the anterior portion 112' is curved and is generally dimensioned to match the curvature of the distal condyle of a native femur. An upper surface 142' of the posterior portion of the base 174 has a generally flat shape and presents a flat surface to the distal condyle of a femur in use. The curved surface 140' and upper flat surface 142' of base 114' generally defines a concave space 144' dimensioned and configured to receive the distal and posterior portions of the condyle of a range of sizes of native femurs owing to the adjustable length of the base portion 114'.

Returning to FIGS. 1 and 2, the cutting guide 100 also includes a handle part 150 which extends laterally and forwardly relative to the curved body 110. The handle part includes a first portion 152 extending laterally from a side of the curved body 110 and a second inclined part 154 which extends forwardly and which terminates in a handle 156 or grip at a free end thereof. The handle extending laterally improves ease of access to the cutting guide 130 and pin holes 132-136 and the handle extending forwardly improves manual handling, including positioning and insertion of the curved body 110 into the native joint gap.

As explained in greater detail below, the cutting guide 100 is used toward the beginning of a unicondylar knee procedure to make a posterior femoral condyle cut with the knee in flexion as the first cut of the procedure. The resected posterior condyle may then be used as a datum surface against which subsequent instrumentation is referenced to make the further femoral and tibial cuts.

Figure 5:
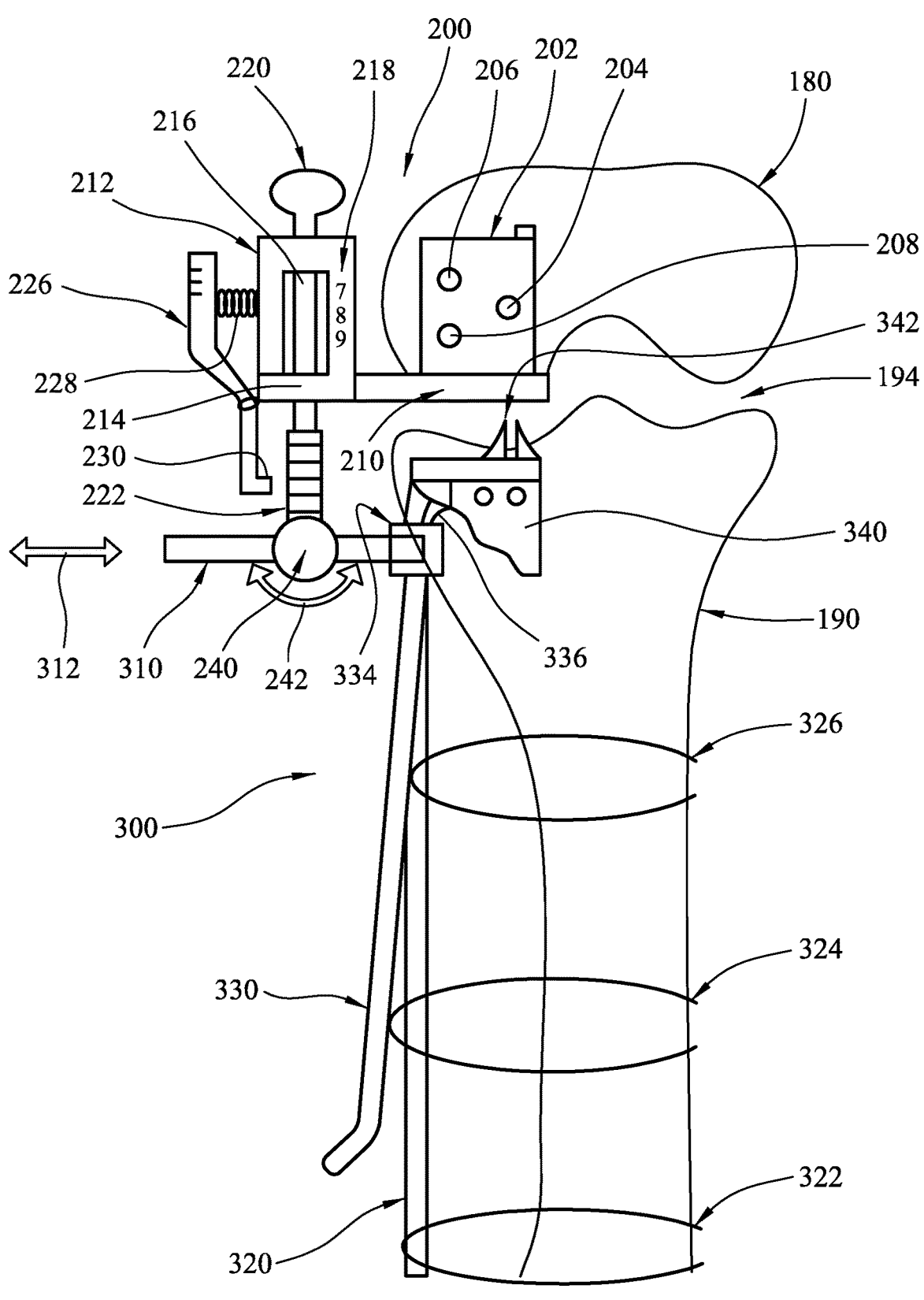
FIG. 5 shows a front elevation of an assembly of a unicondylar tibial reference guide and a unicondylar tibial jig attached to a knee in flexion of a patient.

FIG. 5 shows a front elevation of further unicondylar knee instrumentation that may be used subsequently to the cutting guide 100. The instrumentation shown in FIG. 6 includes a tibial reference guide 200 and a tibial jig 300. The majority of the instrumentation 200 and 300 sits anteriorly of the joint space and also outside the incision or wound space of the patient's knee.

The tibial reference guide 200 and tibial jig are shown mounted on a femur 180 with a resected posterior condyle and a tibia 190 of a patient. The femur is in flexion at an angle of approximately 90 degrees and the joint gap 194 can be seen. The instrumentation 200, 300 is set up for a medial condyle in FIG. 5, but may also be used for a lateral condyle.

The tibial reference guide 200 includes an anterior part 202 generally similar to the anterior part 112 of the cutting guide 100 and having a curved rear surface. First to third pin holes 204, 206, 208 are defined in the anterior part 202 and arranged similarly to those of the cutting block anterior part to receive two straight bone pins 205, 207 and one divergent bone pin (not show). In other embodiments, two divergent bone pins and one straight bone pin, and corresponding pin holes in the instrumentation shown in FIGS. 1 to 4, may be used instead.

The anterior part 202 extends generally upwardly from a base 210 which includes a flat plate extending backwardly from the anterior part 202 and having a flat upper surface which sits flush against the resected posteriori femoral condyle surface. A tower 212 extends upwardly from a lateral part 214 of the base 210 and defines an elongate aperture 216 in a front portion of the tower and having a scale 218 positioned adjacent the aperture 216. A member 220 extends through apertures defined in a top and a bottom part of the tower 212 and has a stop 220 at a first free end and a plurality of grooves or ribs 222 toward a distal end. An arm 226 is pivotally attached to the tower and biased into a locking position by a spring 228 positioned and acting between an upper part of the arm and the tower. A foot 230 at distal a free end of the arm 226 is arranged to interact with a one of the grooves or ribs 222 so as to releasably lock the position of the member 220 relative to the tower 212 and hence relative to the resected posteriori condyle. Arm 226 can be operated to release the foot 230 and thereby allow member 220 to slide relative to the tower 212 so as to adjust the position of the member 220.

The distal end of member 220 includes a pivotable coupling 240. Coupling 240 can rotate within the plane of the sheet of the figure as illustrated by double headed arrow 242. Pivotable coupling 240 also defines a cavity passing there through. An arm 310 of the tibial jig is slidingly received with the cavity of the pivotable coupling 240. Hence arm 310 can be slid relative to pivotable coupling to allow movement of the tibial jig relative to the tibial reference guide 200 in the medial-lateral direction generally, as indicated by double headed arrow 312. It will be appreciated that the sliding axis 312 tilts as coupling 240 is rotated.

Tibial jig 300 includes a main support 320 which is secured to the patient's tibia 190 by a plurality of straps 322, 324, 326. A further arm 330 is pivotally connected to an end of the first arm 310 by a further pivotable coupling 334 which allows the further arm 330 to be pivotable about the longitudinal axis of the first arm 310. A unicondylar tibial cutting block 340 is attached to a top end 336 of further arm 330. The unicondylar tibial cutting block 340 has a body defining at least a first and a second hole for receiving respective bone pins. The body of the unicondylar cutting block 340 also defines a first slot providing a proximal tibial cut guide. A further cutting guide 342 is provided on a top part of the cutting block which provides a sagittal cut guide for making a sagittal cut to the tibia.

The member 216 can be moved to set the tibial cut height relative to the resected posterior femoral condyle, the first pivotable coupling 240 allows the varus/valgus angle of the tibial cut to be set, the slidable arm 310 allows the medial-lateral position of the tibial cutting block to be set and the second pivotable coupling 334 allows second arm 330 to be pivoted to set the anterior-posterior slope of the tibial cutting block to be set.

Pivot 334 may slide longitudinally along member 330, whilst being able to rotate about 2 axes enabling varus/valgus and anterior/posterior slope adjustment. Two separate features may be provided within that section of the jig, such as a ball and socket connection allowing the 2 rotations, and a, for example, D shaped bar and ring to allow vertical sliding.

Hence, the cut height may be adjusted by rotating knob 220, varus-valgus angle (by pivot 240), medial-lateral position (sliding 310 along axis 312) and anterior-posterior slope angle (by the ball and socket type connection and d-ring enabling 334 to slide up and down 330 and rotate) of the tibial cutting block may be set relative to the datum of the resected posterior femoral condyle. The tibial cutting block may then be fixed in place using bone pins and the tibial reference guide 200 removed. The tibial cutting guide may then be used to make the proximal tibial cut and sagittal tibial cut and then the resected tibia may be used as a datum to support a femoral cutting block to further femoral cuts.

Figure 6:
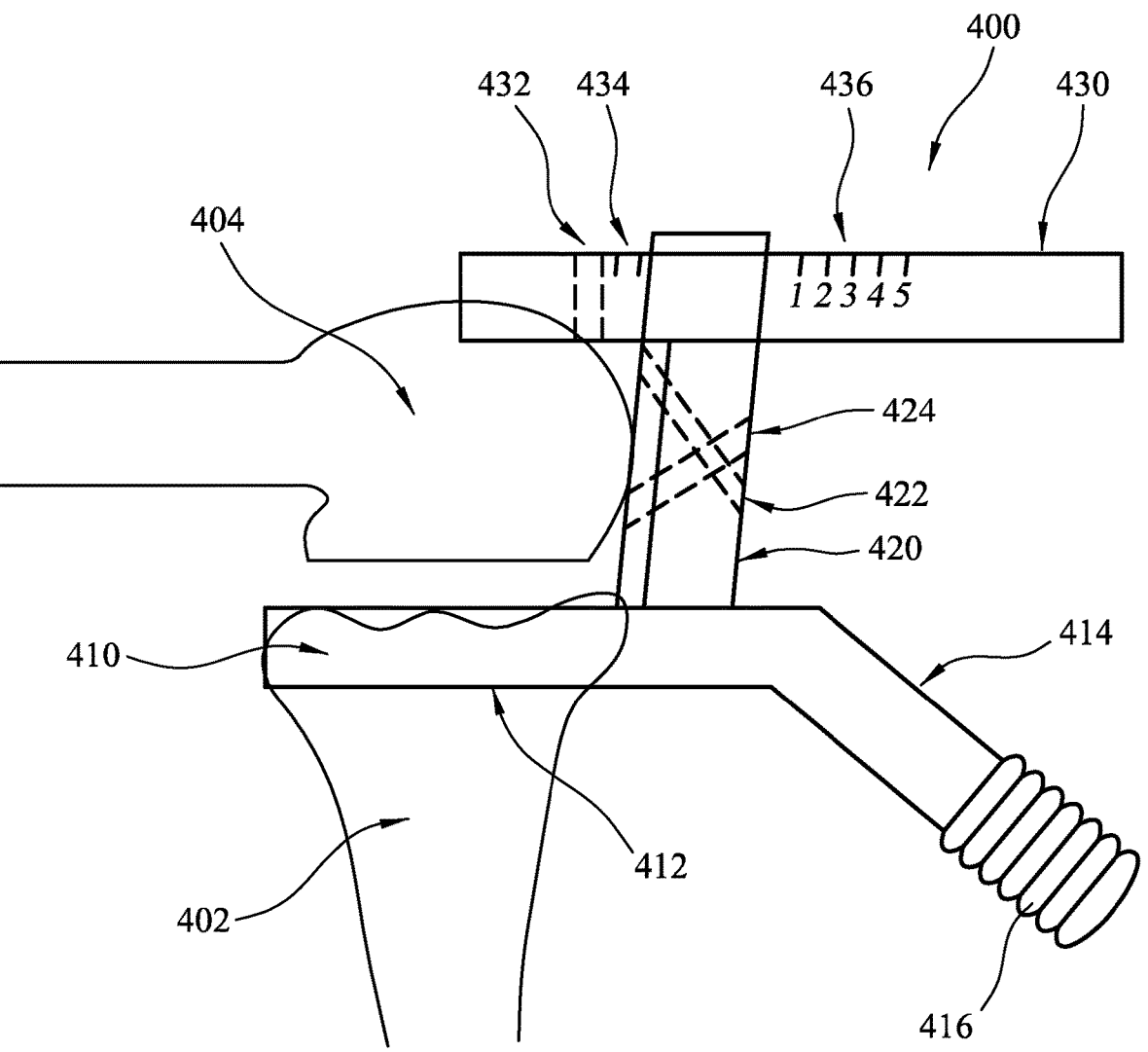
FIG. 6 shows a side elevation of a unicondylar femoral cutting guide attached to the knee in flexion of the patient.

FIG. 6 shows a side elevation of a unicondylar femoral cutting block instrument 400 mounted on the proximal resected tibia 402 and also the femoral condyle 404 with the resected posteriori condyle. The femoral cutting block 400 includes a base 410 having a flat under surface which can sit flush on the resected proximal tibial surface. A handle 414 with a grip 416 at a free end extends forwardly and downwardly from a front end of the base 410. A first end of a removable post 420 is received in a socket in the base 410 and which allows different sized posts to be used with the same base 410. The post 420 defines a first inclined slot 422 and a second inclined slot 424 each of which serves as a chamfer cut guide for making femoral chamfer cuts as a generally known in the art. A plurality of posts generally similar to post 420 may be provided having different lengths to accommodate different sized femurs and having the chamfer cut guide slots at increasing separation (with increasing post size) as the location of the chamfer cuts will change with the size of the femur.

A second end of the post 420 defines a further aperture therein which slidingly receives a member 430. Member 430 defines a slot 432 extending generally perpendicularly to the longitudinal axis of the member and generally parallel to the longitudinal axis of post 420. Slot 432 provides a distal femoral cut guide for making the distal femoral cut. Member 430 also includes a first scale 434 closer to the distal cut slot 432 and a second scale 436 further from the distal cut slot. As the member 430 is slidable relative to post 420, the position of the distal cut slot relative to the femur may be adjusted to allow the distal cut to be distalised (moved closer to the most distal part of the native femur, i.e. made more distal) or proximalised (moved further away from the most distal part of the femur, i.e. made more proximal). Distalising or proximalising the position of the distal femoral cut may be desirable to improve joint balance by making the gap joint more similar for the knee in flexion and extension, as described in greater detail below. Hence, first scale 434 provides a quantitative measure of how much the cut position has been distalised and second scale 436 provides a quantitative measure of how much the cut position has been proximalised by sliding the member 430 relative to post 420. The gradations of scale 434 and 436 may be, for example, 1 mm.

Hence, the unicondylar femoral cutting block instrument 400 may be used to make the distal femoral cut and up to two chamfer femoral cuts, depending on the number of chamfer cuts used by the implant system.

Having described the various pieces of unicondylar instrumentation, the general method of use of the instrumentation as part of a unicondylar knee replacement surgical procedure will now be described in greater detail with reference to FIG. 7.

FIG. 7 shows a flow chart illustrating a unicondylar or partial knee replacement procedure 500 and including various methods of use of the surgical instrumentation described above. Many of the steps of the procedure are conventional and hence have either been omitted or are described briefly in order not to obscure the present disclosure.

At 502 the patient's exposed knee is place in flexion and the surgeon may assess the size of the femoral condyle being replaced, either the medial or the lateral condyle. As noted above the cutting guide 100 may be provided in a number of different sizes. A common releasable handle 150 may be provided which is releasably attachable to different sized curved bodies 110. The curved bodies may have a plurality of different lengths in the anterior-posterior direction and each different anterior-posterior size may have a plurality of different widths in the medial-lateral direction. Hence, the surgeon selects a curved body most closely matching the anterior-posterior size and medial-lateral size of the patient's condyle. The curved body is then attached to the handle 150 and the free end of the curved base 114 is inserted into the knee joint, which typically has a width of approximately 2 mm to 3 mm, at 504. The knee may be placed in greater than 90° of flexion in order to ease insertion of the cutting guide. Once the curved body is inserted in the knee joint it is first generally aligned with the tibial mechanical axis by manipulating the handle until the longitudinal axis of the grip is generally parallel to the mechanical axis of the tibia. The curved body is then urged against the posterior femoral condyle until it seats on the minimum region 116 of the upper surface 142 of the curved based 114. Optionally, where the tail portion 120 is provided, the curved body may then be pulled in an anterior direction until the tail 120 engages the posterior condyle and resists further anterior movement of the cutting guide.

The cutting guide may then be pinned in place using two parallel bone pins and a divergent bone pin passing through fixation holes 132, 134, 136. Handle 150 may then be removed and then the posterior femoral condyle cut may be made at 506 by passing a cutting instrument, such as a chisel or saw, through the cutting guide slot 130. Hence, in this procedure 500, the posterior femoral condyle cut is done first as often this may be where the best bone stock is located and hence may provide the most reliable datum surface from which subsequent steps of the procedure may be referenced. The divergent pin is then removed and the curved cutting body 110 is removed by being slid over the two parallel bone pins which may be left in place. At 508 the tibial reference guide 200 is mounted on the partially resected femur by sliding the anterior portion 202 over the two parallel bone pins 205, 207 which may pass through holes 206 and 208 and with the rear flat plate of the reference guide abutting the resected posteriori femoral condyle. The reference guide 200 may then be fixed in place by inserting a divergent bone pin through third pin hole 204.

At 510 the tibial jig 300 may be strapped to the patient's tibia and coupled to the tibial reference guide 200. The assembled instrumentation may then be used to set the position and orientation of the tibial cutting block 340. This may include one or more of operating the arm 226 to allow the member 216 to be moved relative to the tower 218 to allow the tibial cut height to be set at some preferred joint gape value which may be read from scale 218. Also, the varus-valgus angle of the tibial cut may be adjusted using pivotable coupling 240. Also, the medial-lateral position of the tibial cutting block may be adjusted using slidable rod 310. Also, the anterior-posterior slope angle may be adjusted using further pivotable coupling 334. The tibial cutting block 340 may then be pinned in place and the tibial support jig 300 may be removed before the tibial transverse cut and the tibial sagittal cut are made using the slots of the tibial cutting block to guide the cutting instrument. The tibial cutting block 340 and the tibial reference guide 200 may then be removed.

At 514 the balance of the gaps in flexion and extension are assessed and noted in a generally conventional way by placing the knee in flexion and extension and measuring the gap in flexion and the gap in extension. If the extension gap is greater than the flexion gap, then the distal femoral cut may be distalised to reduce the difference. Similarly, if the flexion gap is greater than the extension gap, then the distal femoral cut may be proximalised to reduce the difference. At 516 the tibial stabilising base part 410 of the tibial cutting guide 400 is obtained and a suitably sized post 420 for the prosthetic femoral implant to be used on the patient's femur is selected and attached to the stabilising base 410. The tibial cutting guide 400 is located in the resected joint space with the stabilising base 410 mounted on the resected tibia. The member 430 may then be slid relative to post 420 to locate the distal cutting slot 432 at the correct position. The scale 436 may be used to set any amount of distalisation of the distal cut (e.g. 2 mm, if the extension gap was 2 mm greater than the flexion gap) or the scale 434 may be used to set any amount of proximalisation (e.g. 1 mm, if the extension gap was 1 mm less than the flexion gap).

Once the distal cut slot 432 has been appropriately positioned at 516, then the distal femoral cut may be made at 518 using the distal femoral cut slot 432 to guide the cutting instrument. The slidable member 430 may then be removed and at 520 up to two chamfer cuts may be made (dependent on the implant) using the first 422 and/or second 424 chamfer cut slots in the post 420 of the femoral cutting block 400. Hence, the femoral posterior, distal and up to two chamfer cuts have been made. The rest of the unicondylar knee procedure may then proceed in a generally conventional manner as indicated by 522.

Hence, the unicondylar knee procedure 500 uses a posterior femoral condyle cut first, with the knee in flexion, in order to use the good bone on the posterior condyle to provide a reliable datum from which subsequent parts of the procedure are referenced.

In this specification, example embodiments have been presented in terms of a selected set of details. However, a person of ordinary skill in the art would understand that many other example embodiments may be practiced which include a different selected set of these details. It is intended that the following claims cover all possible example embodiments.

Any instructions and/or flowchart steps can be executed in any order, unless a specific order is explicitly stated. Also, those skilled in the art will recognize that while one example set of instructions/method has been discussed, the material in this specification can be combined in a variety of ways to yield other examples as well, and are to be understood within a context provided by this detailed description.

While the disclosure is amenable to various modifications and alternative forms, specifics thereof have been shown by way of example in the drawings and described in detail. It should be understood, however, that other embodiments, beyond the particular embodiments described, are possible as well. All modifications, equivalents, and alternative embodiments falling within the scope of the appended claims are covered as well.

The invention claimed is:

1. Instrumentation for a unicondylar knee replacement procedure, comprising:

a unicondylar posterior femoral cutting guide including a guide body having an anterior guide portion and a guide base, the anterior guide portion and the guide base defining a curved inner surface dimensioned to match a curvature of a condyle of a patient's native femur, the anterior guide portion defines a slot arranged to guide a unicondylar posterior femoral cut to create a resected surface of the patient's femur;

a tibial reference guide; and a tibial jig, wherein the tibial reference guide comprises an anterior portion having a curved inner surface, a base extending from the anterior portion and having a flat upper surface defining a reference plane, the flat upper surface being configured to engage the resected surface of the patient's femur, and a coupling mechanism for connecting the tibial reference guide to the tibial jig, wherein the tibial jig includes a support attachable to a tibia of a patient, an attachment formation for attaching a unicondylar tibial cutting block and a coupling member arranged to connect to the coupling mechanism, and wherein the tibial reference guide and the tibial jig provide between them a first adjustment mechanism including a housing and an elongate member which is slidable relative to the housing to adjust the separation between the tibial reference guide and the tibial jig in a direction perpendicular to the reference plane when the tibial reference guide and tibial jig are connected together.

2. Instrumentation as claimed in claim 1, wherein the anterior portion defines a plurality of apertures there through for receiving respective bone pins to permit fixation of the tibial reference guide to a femur of the patient in use.

3. Instrumentation as claimed in claim 2, wherein the plurality of apertures comprises a first aperture, a second aperture and a third aperture, and wherein the first aperture and second aperture are parallel to each other and the third aperture is inclined relative to the first and second apertures.

4. Instrumentation as claimed in claim 1, wherein the first adjustment mechanism comprises a releasable lock which is operable to set the position of the elongate member relative to the housing.

5. Instrumentation as claimed in claim 1, wherein the housing includes a scale and the elongate member includes an indicium adjacent the scale and arranged to indicate a current separation value for a current position of the elongate member relative to the housing.

6. Instrumentation as claimed in claim 1, wherein the first adjustment mechanism is provided as part of the tibial reference guide.

7. Instrumentation as claimed in claim 6, wherein the first adjustment mechanism is attached to the base of the tibial reference guide and is positioned to the side of the rest of the tibial reference guide.

8. Instrumentation as claimed in claim 1, wherein the tibial reference guide and the tibial jig provide between them a second adjustment mechanism arranged and configured to adjust the varus-valgus angle of the tibial jig relative to the tibial reference guide.

9. Instrumentation as claimed in claim 1, wherein the tibial reference guide and the tibial jig provide between them a third adjustment mechanism arranged and configured to adjust the medial-lateral position of the tibial jig relative to the tibial reference guide.

10. Instrumentation as claimed in claim 1, wherein the guide base of the unicondylar posterior femoral cutting guide includes an adjustment mechanism having a plurality of gears operable to change the anterior-posterior length of the guide base, the guide base including a portion of the curved inner surface dimensioned to match a curvature of a posterior portion of the condyle of the patient's native femur.

* * * * *